US010520422B2

(12) United States Patent
 Chiu et al.

(10) Patent No.: US 10,520,422 B2
(45) Date of Patent: Dec. 31, 2019

(54) OPTICAL MICRO-PARTICLES DETECTOR

(71) Applicant: Industrial Technology Research Institute, Hsinchu (TW)

(72) Inventors: Wei-Lan Chiu, Kaohsiung (TW); Hsiang-Hung Chang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 75 days.

(21) Appl. No.: 15/842,889

(22) Filed: Dec. 15, 2017

(65) Prior Publication Data
 US 2019/0072476 A1 Mar. 7, 2019

(30) Foreign Application Priority Data
 Sep. 7, 2017 (TW) .............................. 106130689 A

(51) Int. Cl.
 *G01N 15/14* (2006.01)
 *G01N 15/02* (2006.01)
 *G01N 15/00* (2006.01)
(52) U.S. Cl.
 CPC ..... *G01N 15/1434* (2013.01); *G01N 15/0211* (2013.01); *G01N 15/1404* (2013.01); *G01N 15/1436* (2013.01); *G01N 15/1459* (2013.01); *G01N 15/1484* (2013.01); *G01N 2015/0046* (2013.01); *G01N 2015/035* (2013.01); *G01N 2015/1447* (2013.01); *G01N 2015/1486* (2013.01)
(58) Field of Classification Search
 CPC .................................................. G01N 15/1434
 USPC ............................................................ 356/340
 See application file for complete search history.

(56) References Cited

U.S. PATENT DOCUMENTS

| 4,556,318 | A | * | 12/1985 | Barnes | .................... | G01N 21/74 356/316 |
| 5,726,751 | A | | 3/1998 | Altendorf et al. | | |
| 5,946,091 | A | * | 8/1999 | Yufa | ................... | G01N 15/0205 356/336 |
| 6,519,033 | B1 | * | 2/2003 | Quist | ...................... | G01N 15/14 356/337 |
| 7,057,724 | B1 | * | 6/2006 | Mead | ................. | G01N 15/1459 356/343 |
| 8,867,035 | B2 | | 10/2014 | Nicoletti | | |

(Continued)

FOREIGN PATENT DOCUMENTS

EP        1801563        6/2007

OTHER PUBLICATIONS

"Office Action of Taiwan Counterpart Application", dated May 25, 2018, p. 1-p. 4.

(Continued)

*Primary Examiner* — Tarifur R Chowdhury
*Assistant Examiner* — Omar H Nixon
(74) *Attorney, Agent, or Firm* — JCIPRNET

(57) ABSTRACT

An optical micro-particle detector including a light source, a gas channel and a plurality of optical detectors is provided. The light source is configured to generate a light beam. The gas channel has at least one curved segment. The curved segment has a light entrance and a plurality of light exits. The light beam from the light source enters the gas channel through the light entrance. The plurality of optical detectors are optically coupled to the light exits, respectively.

22 Claims, 12 Drawing Sheets

(56) References Cited

U.S. PATENT DOCUMENTS

| | | | |
|---|---|---|---|
| 8,941,826 B2 | 1/2015 | Nawaz et al. | |
| 9,464,977 B2 | 10/2016 | Di Carlo et al. | |
| 9,588,289 B1 | 3/2017 | Astier et al. | |
| 2003/0035105 A1* | 2/2003 | Quist | G01N 15/14 356/338 |
| 2004/0105163 A1* | 6/2004 | Bryan | G02B 6/124 359/652 |
| 2005/0195605 A1* | 9/2005 | Saccomanno | G01N 15/1459 362/268 |
| 2009/0153857 A1 | 6/2009 | Matsuda | |
| 2011/0223586 A1 | 9/2011 | Karabinus | |
| 2012/0105839 A1* | 5/2012 | Novosselov | G01N 1/2208 356/301 |
| 2012/0257193 A1* | 10/2012 | Hummel | B01F 13/0066 356/73.1 |
| 2014/0368820 A1* | 12/2014 | Sugasawa | G01N 15/0211 356/336 |

OTHER PUBLICATIONS

Wenjia Shao, et al., "Fine Particle Sensor Based on Multi-Angle Light Scattering and Data Fusion," Sensors, May 4, 2017, pp. 1-16.

Xuming Gao, "Development of Cellphone Integrated Particulate Matter Pollution Monitoring Unit," Program of Mechanical Engineering, Ryerson University, 2015, pp. 1-64.

Hai-Dong Kan, et al., "Establishment of Exposure-response Functions of Air Particulate Matter and Adverse Health Outcomes in China and Worldwide," Biomedical and Environmental Sciences, vol. 18, Jun. 2005, pp. 159-163.

Andre Nel, "Air Pollution-Related Illness: Effects of Particles," Science, vol. 308, May 6, 2005, pp. 804-806.

David W. Hahn, "Light Scattering Theory," Department of Mechanical and Aerospace Engineering, Florida, Jul. 2009, pp. 1-13.

Biqin Dong, et al., "Real-time Functional Analysis of Inertial Microfluidic Devices via Spectral Domain Optical Coherence Tomography," Scientific Reports, Sep. 2016, pp. 1-10.

Virgil A. Marple, et al., "Virtual Impactors: A Theoretical Study," Environmental Science and Technology, vol. 14, Aug. 1980, pp. 976-985.

Yong-Ho Kim, et al., "A hybrid chip based on aerodynamics and electrostatics for the size-dependent classification of ultrafine and nano particles," Lab on a Chip, Jul. 1, 2009, pp. 2722-2728.

"Office Action of Taiwan Counterpart Application", dated Oct. 29, 2018, p. 1-p. 6.

* cited by examiner

OPTICAL MICRO-PARTICLES DETECTOR

CROSS-REFERENCE TO RELATED APPLICATION

The present application is based on, and claims priority from, Taiwan Application Serial Number 106130689, filed on Sep. 7, 2017. The entirety of the above-mentioned patent application is hereby incorporated by reference herein.

TECHNICAL FIELD

The disclosure relates to an optical micro-particle detector.

BACKGROUND

In recent years, fine suspended particulate matter (PM2.5) becomes an important environmental air pollution problem in the world. If people exposed themselves to the polluted environment for a long time, the people will be under the risk of lung cancer, stroke, heart disease, chronic respiratory disease, respiratory infections and asthma and other diseases. PM2.5 pollution is a significant impact on human health. Therefore, the detectable PM 2.5 machine becomes more important. The existing PM2.5 detectors are, for example, weighted type detectors or optical type detectors.

However, the weighted type detector is heavy and expensive. The accuracy of optical type detector is not good enough. Also, the optical type detector fails to be integrated with the chip directly, and needs a fan to provide air flow.

SUMMARY

According to an embodiment of the present disclosure, an optical micro-particle detector is provided. The optical micro-particle detector includes a light source, a gas channel and a plurality of optical detectors. The light source generates a light beam. The gas channel has at least one curved segment. The at least one curved segment has a light entrance and a plurality of light exits. The light beam from the light source passes through the light entrance and enters the gas channel. The plurality of optical detectors are optically coupled to the plurality of light exits, respectively.

The foregoing will become better understood from a careful reading of a detailed description provided herein below with appropriate reference to the accompanying drawings.

DETAILED DESCRIPTION OF DISCLOSED EMBODIMENTS

Figure 1:
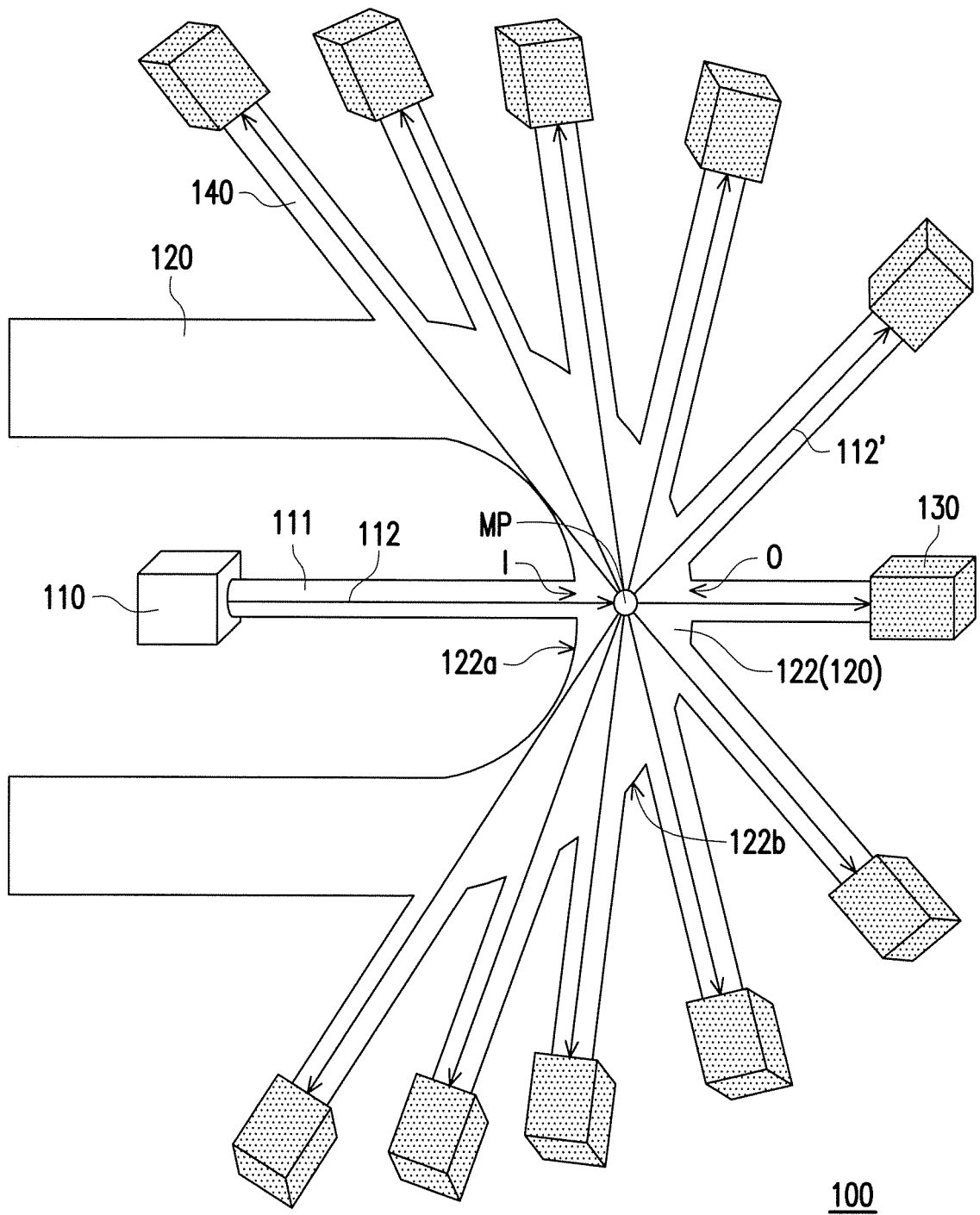
FIG. 1 is a top view of an optical micro-particle detector according to an embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

FIG. 1 is a top view of an optical micro-particle detector according to an embodiment of the disclosure. Refer to FIG. 1, an optical micro-particle detector 100 may include a light source 110, a gas channel 120 and a plurality of optical detectors 130. The light source 110 generates a light beam 112. The gas channel 120 has at least one curve segment 122. The at least one curve segment 122 has a light entrance I and a plurality of light exits O. There is a light channel 111 between the light source 110 and the light entrance I wherein the light beam 112 from the light source 110 passes through the light channel 111, reaches the light entrance I and enters the gas channel 120. The plurality of optical detectors 130 are optically coupled to the plurality of the light exits O, respectively. In this embodiment, the optical micro-particle detector further includes a plurality of light channels 140. The plurality of the light channels 140 are optically coupled between the plurality of optical detectors 130 and the plurality of light exits O of the gas channel 120, respectively. Also, the plurality of the light channels 140 extend radially. After the light beam 112 from the light source 110 passes through the light entrance I and enters the gas channel 120, if the light beam 112 strikes a micro particles MP, a plurality of light beam 112' may be scattered in different directions due to a Mie scattering occurrence. Then, the plurality of light beams 112' in different directions enter the plurality of the light channels 140 through the plurality of light exits O, respectively, and the plurality of light beams 112' are incident on the plurality of the optical detectors 130. In this embodiment, the light source 110 may be a laser or a light-emitting diode (LED). The plurality of the optical detector 130 may be a photodiode (for example, a GaAsP photodiode) or a Silicon P-intrinsic-N photodiode, Silicon PIN photodiode, or Phototransistor, or other photodetectors.

In the embodiment, the gas channel 120 has a curved segment 122, and the curved segment 122 has the plurality of light exits O which are optically coupled to the plurality of optical detectors 130. Therefore, when the light beam 112 strikes the micro particles in the curved segment 122, the light beams 112' along the path of the light beam 112 can be detected by at least one of the plurality of the optical detectors 130. In addition, the light beams 112' in lateral directions can be effectively detected by other optical detectors 130 in the lateral directions. Since the curved segment 122 of the gas channel 120 is a curved design, more optical detectors 130 can be placed, and the curved design shortens the distances between these optical detectors 130 in the lateral directions and micro particles so that the light beams 112' in the lateral directions are less likely to strikes other micro particles before reaching the light exits O in the lateral directions and increase the accuracy of the light beam measurement. Therefore, the measurement accuracy of the optical micro-particle detector 100 can be increased.

In this embodiment, the curve segment 122 of the gas channel 120 has a first side wall 122a and a second side wall 122b. The first side wall 122a is opposed to the second side wall 122b. The light entrance I is located on one of the first side wall 122a and the second side wall 122b. The plurality of light exits O are located on one of the first side wall 122a and the second side wall 122b. As shown in FIG. 1, the light entrance I is located on the first side wall 122a and the plurality of light exits O are located on the second side wall 122b. In an embodiment (not shown), the light entrance I may be located on the second side wall 122b and the plurality of light exits O may be located on the first side wall 122a. In another embodiment, the light entrance I may be located on the first side wall 122a or the second side wall 122b, and some of the plurality of light exits O may be located on the first side wall 122a, and other light exits O may be located on the second side wall 122b, but the scope of the disclosure is not limited thereto.

Figure 2:
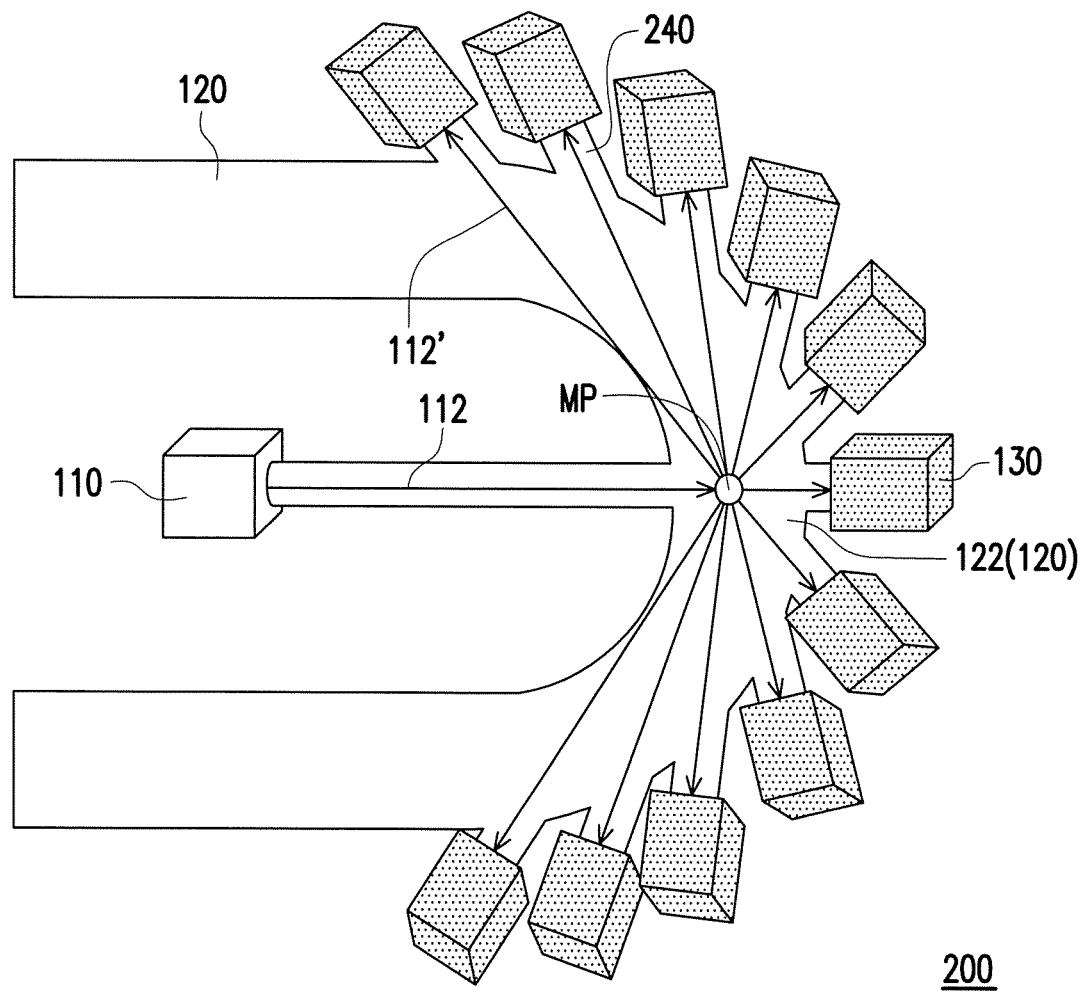
FIG. 2 is a top view of an optical micro-particle detector according to an embodiment of the disclosure.

FIG. 2 is a top view of an optical micro-particle detector according to an embodiment of the disclosure. The optical micro-particle detector 200 in FIG. 2 and the optical micro-particle detector 100 in FIG. 1 are similar. The difference is that the light channel 240 of the optical micro-particle detector 200 is shorter so that the optical detector 130 is closer to the light exits O. Therefore, the light beam 112' has a shorter scattering path before being incident on the optical detector 130. This prevents an energy loss of the light beams 112' during light scattering.

Figure 3:
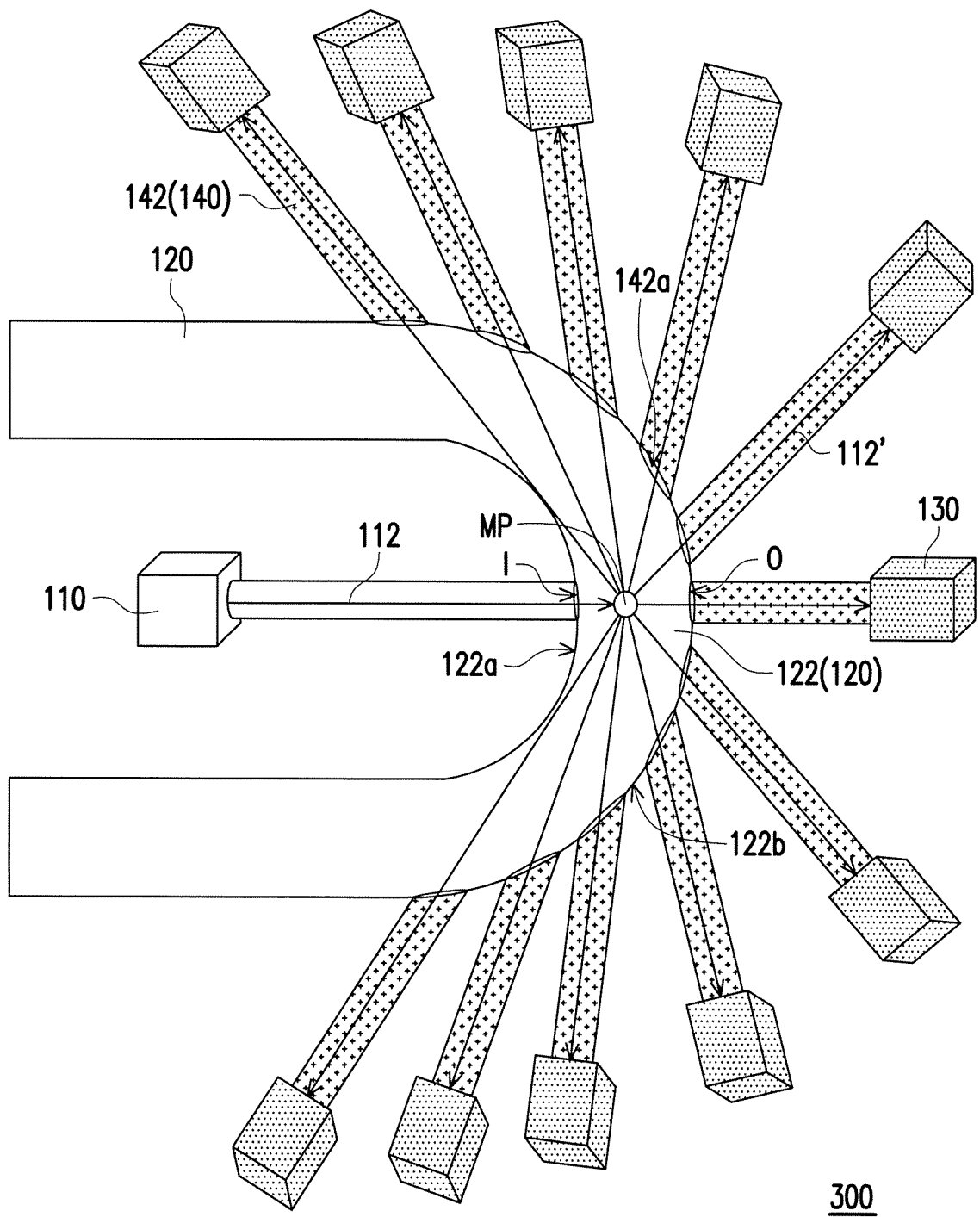
FIG. 3 is a top view of an optical micro-particle detector according to an embodiment of the disclosure.

FIG. 3 is a top view of an optical micro-particle detector according to an embodiment of the disclosure. The optical micro-particle detector 300 in FIG. 3 and the optical micro-particle detector 100 in FIG. 1 are similar. The difference is that each of the plurality of the light channels 140 of the optical micro-particle detector 300 includes an optical waveguide 142. The optical waveguide 142 is disposed in the light channel 140 and extends along an extending direction of the light channel 140. In the embodiment of FIG. 3, each of light channels 140 includes the optical waveguide 142. This prevents an energy loss during the light beams 112' scattering the light channels 140. In the embodiment of FIG. 3, the material of the optical waveguide 142 may be a photoresist (for example, SU-8 photoresist) or a material transparent or light-emissive to the light beam 112'.

Figure 4:
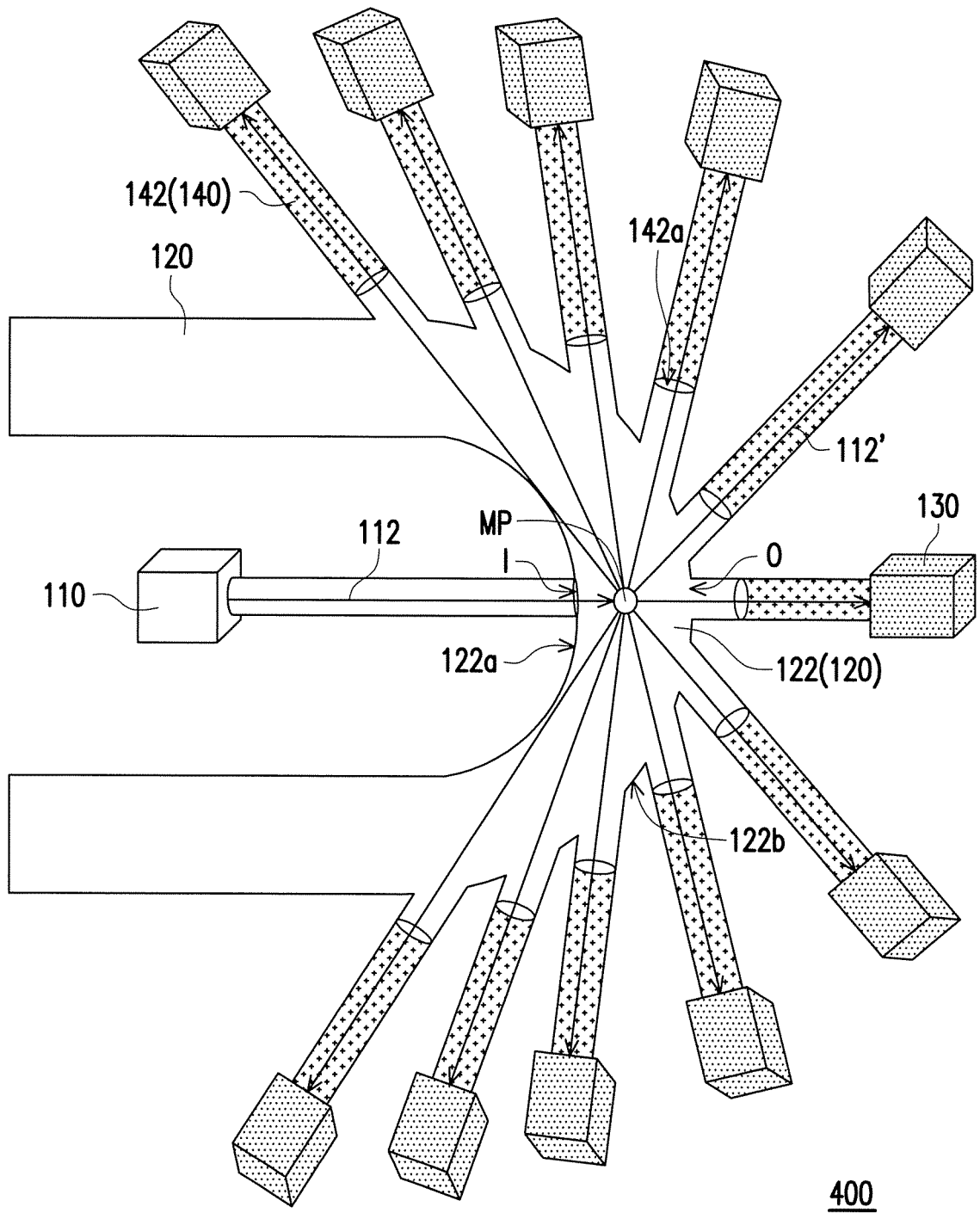
FIG. 4 is a top view of an optical micro-particle detector according to an embodiment of the disclosure.

FIG. 4 is a top view of an optical micro-particle detector according to an embodiment of the disclosure. The optical micro-particle detector 400 in FIG. 4 and the optical micro-particle detector 100 in FIG. 1 are similar. The difference is that the optical waveguide 142 of the optical micro-particle detector 400 includes a light entrance surface 142a. The light entrance surface 142a is located near a side of the gas channel 120. Also, the light entrance surface 142a is located on an inner side of the light channel 140 and keeps a distance from its corresponding light exit O. As shown in the optical micro-particle detector 300 of FIG. 3, the light entrance surface 142a of the optical waveguide 142 is located on its corresponding light exit O, and the light beams 112' at any angle may be incident on the optical waveguide 142. As shown in the optical micro-particle detector 400 of FIG. 4, the light entrance surface 142a of the optical waveguide 142 is located on the inner side of the light channel 140 and keeps a distance from its corresponding light exit O. In FIG. 4, only a part of the light beam 112' closely parallel to an extending direction of the light channel 140 may be incident on the optical waveguide 142, and the light beams 112' at other angles fail to be incident on the optical waveguide 142. Therefore, this may prevent the interference of incident beams at other angles during the beam measurement.

Figure 5:
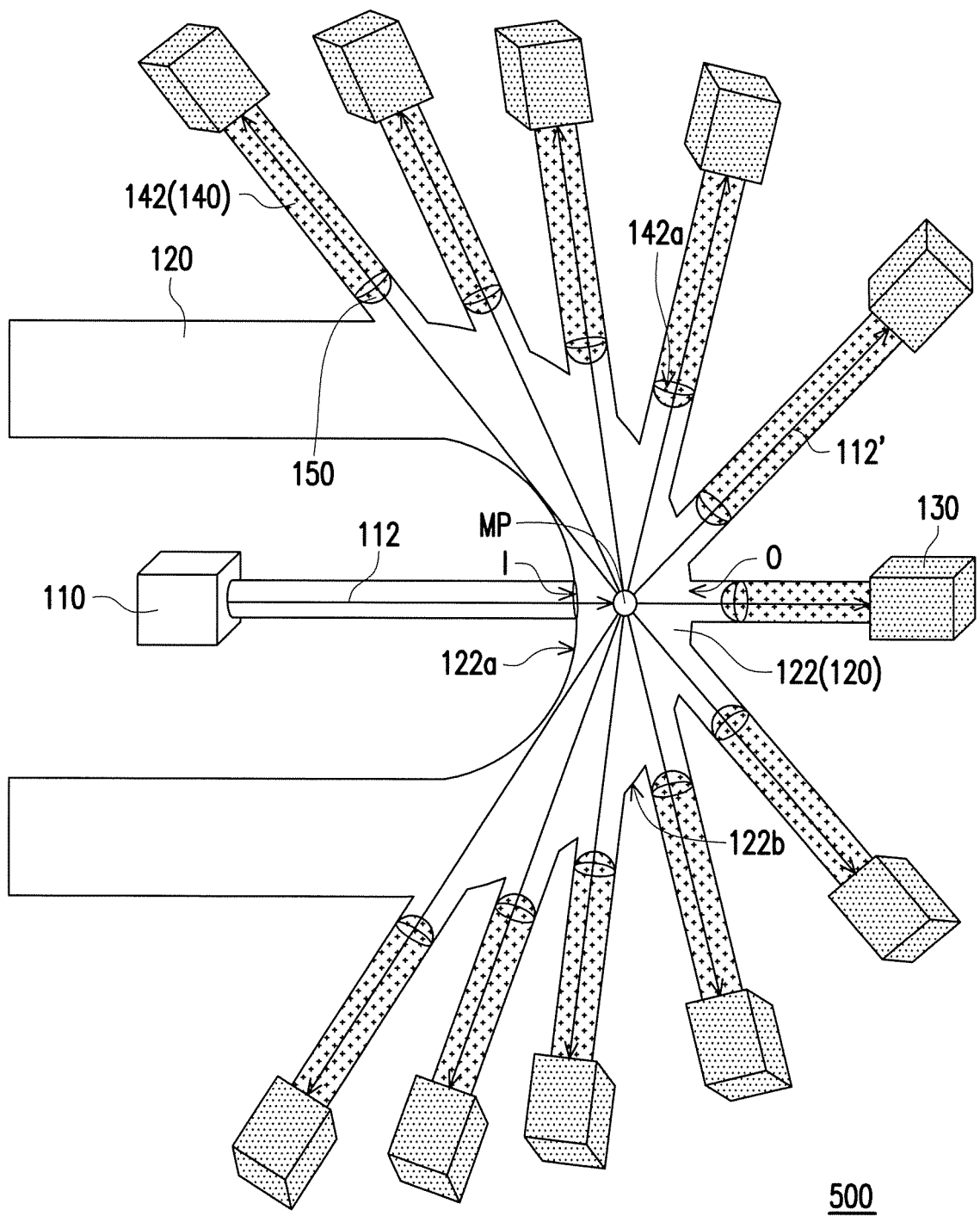
FIG. 5 is a top view of an optical micro-particle detector according to an embodiment of the disclosure.

FIG. 5 is a top view of an optical micro-particle detector according to an embodiment of the disclosure. An optical micro-particle detector 500 in FIG. 5 and the optical micro-particle detector 400 in FIG. 4 are similar. The difference is that a focus lens 150 is disposed in the optical waveguide 142 of the optical micro-particle detector 500. The focus lens 150 is near the gas channel 120 and is integrated with the optical waveguide 142.

Figure 6:
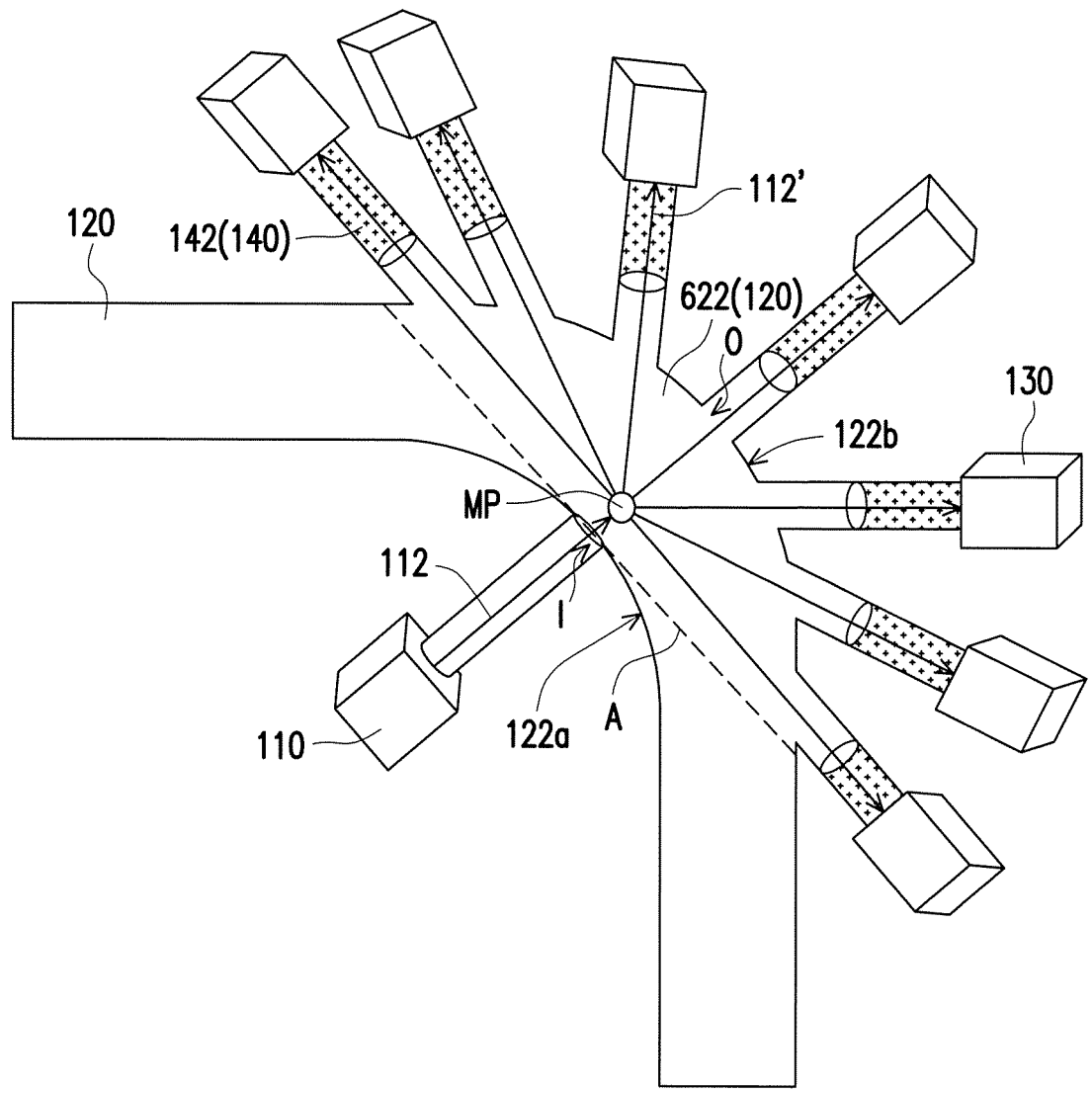
FIG. 6 is a top view of an optical micro-particle detector according to an embodiment of the disclosure.

FIG. 6 is a top view of an optical micro-particle detector according to an embodiment of the disclosure. The optical micro-particle detector 600 in FIG. 6 and the optical micro-particle detector 400 in FIG. 4 are similar. The curved segment 122 of the gas channel 120 shown in FIG. 4 is 180° arc-shaped (U-shaped). In the optical micro-particle detector 600 of FIG. 6, a curved segment 622 of the gas channel 120 is 90° arc-shaped (L-shaped). In the embodiment of FIG. 6, a disposition range of the plurality of the light exits O in the curved segment 622 is within the intersections of a tangent plane A and the second side wall 122b, wherein the tangent plane A is taking the light entrance I as a point of tangency. In other words, the disposition range of the plurality of light exits O in the curved segment 622 is between the intersections of the tangent plane A and the second side wall 122b.

Figure 7:
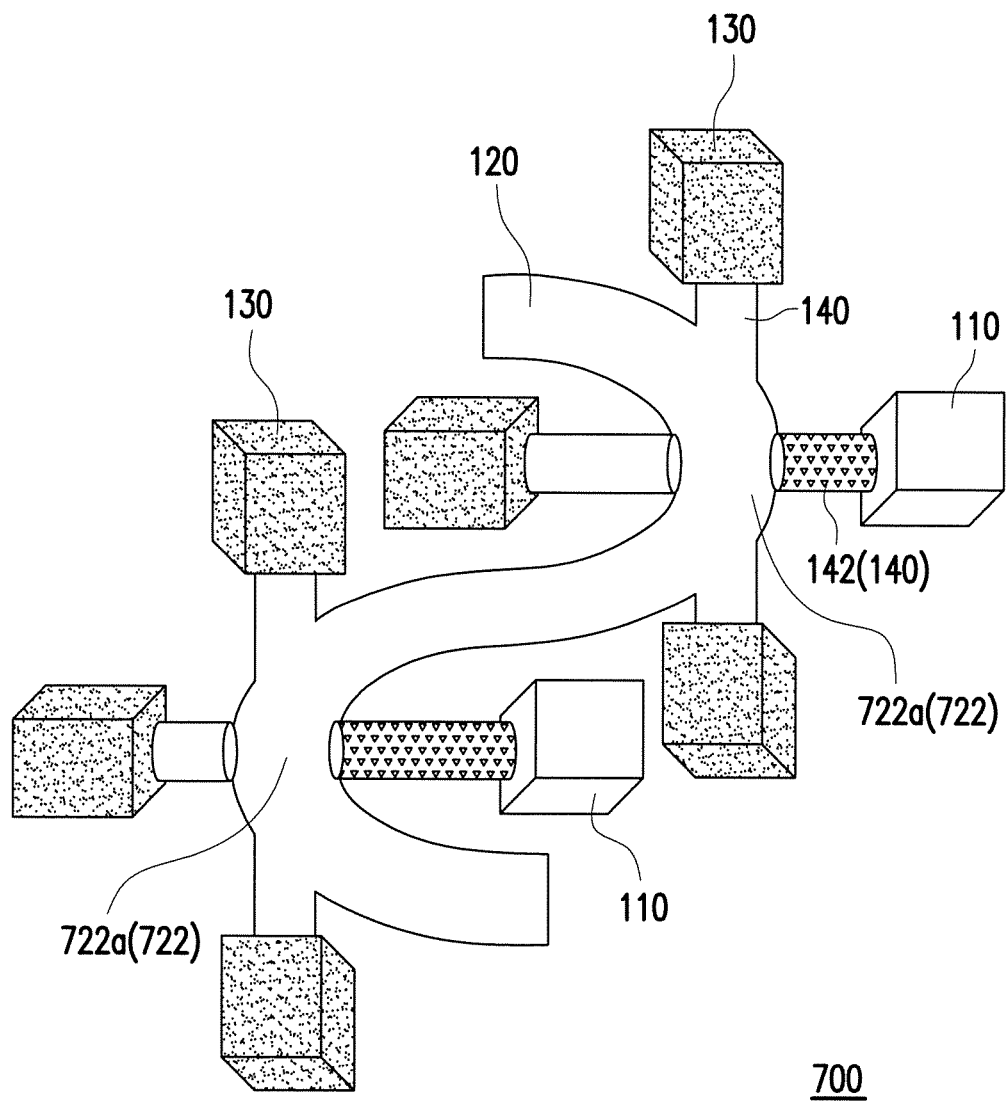
FIG. 7 is a top view of an optical micro-particle detector according to an embodiment of the disclosure.

FIG. 7 is a top view of an optical micro-particle detector according to an embodiment of the disclosure. Refer to FIG. 7, at least one curved segment 722 of the gas channel 120 may be a plurality of connected curved segments 722a in the optical micro-particle detector 700 (for example, two curved segments 722a in FIG. 7). Curved directions of every two adjacent connected curved segments 722a are different from each other. In the embodiment of FIG. 7, some of the plurality of the light channels 140 may include the optical waveguides 142 while other light channels 140 may not. In another embodiment, all of the plurality of the light channels 140 include optical waveguides 142, or none of the plurality of the light channels 140 include the optical waveguide 142.

Figure 8A:
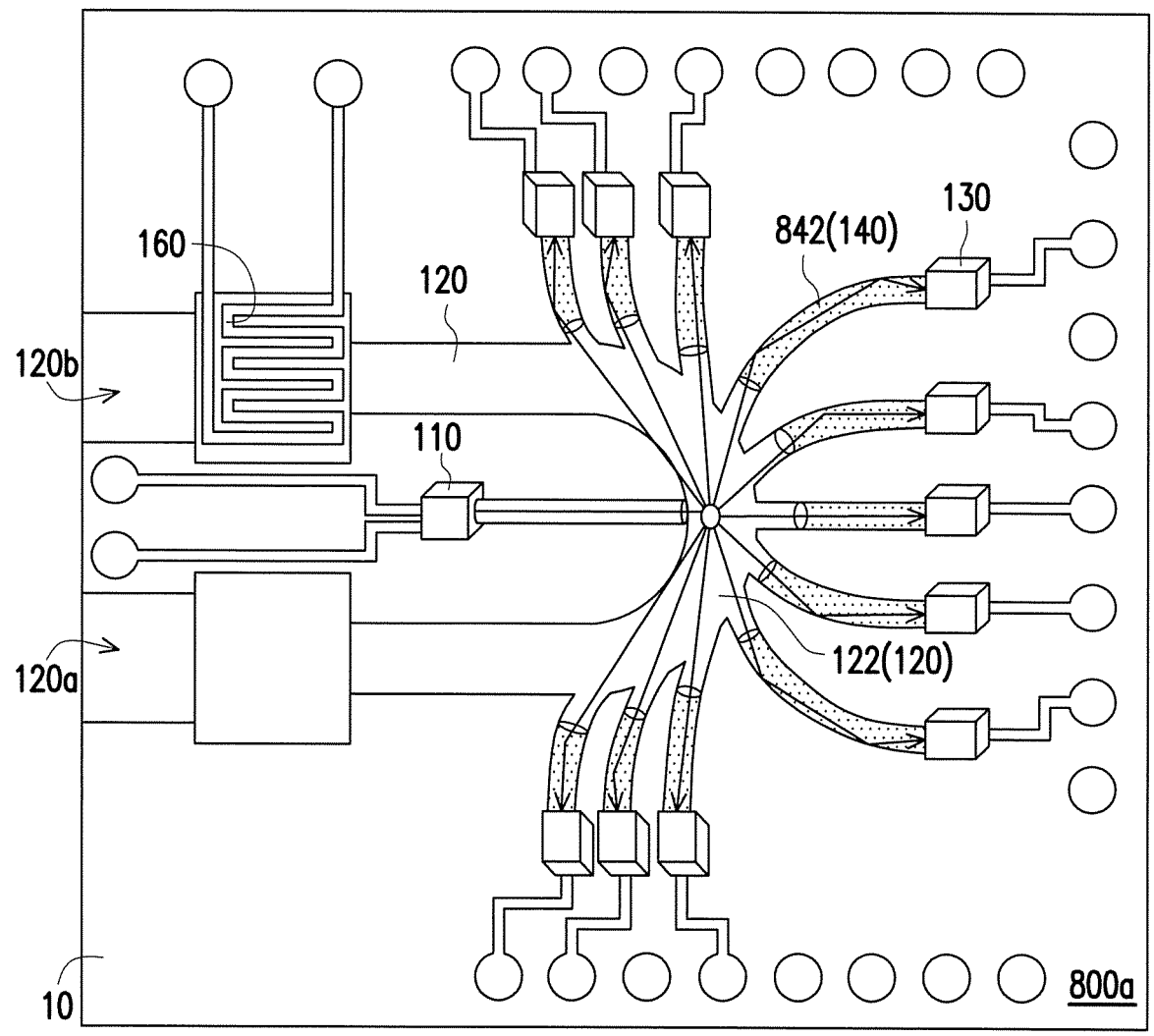
FIG. 8A is a top view of an optical micro-particle detector according to an embodiment of the disclosure.

FIG. 8A is a top view of an optical micro-particle detector according to an embodiment of the disclosure. The optical micro-particle detector 800a in FIG. 8A and the optical micro-particle detector 400 in FIG. 4 are similar. The difference is that a plurality of optical waveguides 842 may be curved in the optical micro-particle detector 800a, to have the plurality of the optical detectors 130 being close to the edge of the substrate 10. The optical micro-particle detector 800a further includes a heating device 160. The heating device 160 may be, for example, a heating coil. The heating device is disposed in or beside the gas channel 120. In detail, since the plurality of optical waveguides 842 may guide the light beam through a total reflection principle, the plurality of optical waveguides 842 is not limited to a linear design. Also, the loss energy of the light beam during scattering in the optical waveguides 842 is not easily occurred, so that the plurality of optical waveguides 842 can extend to a farther location. In other word, the plurality of optical waveguides 842 may be curved and the position of the plurality of the optical detectors 130 may be arranged in accordance with the size of the chip to increase the flexibility of the design. Furthermore, since the plurality of optical detectors 130 may be disposed at the edge of the substrate 10, the plurality of the optical detectors 130 may be connected to external circuits without complicated wiring. This facilitates the integration of the chip. Besides, in the embodiment, the heating device 160 is disposed at a gas outlet 120b near the gas channel 120 for heating the gas flowing in the gas channel 120, so that the gas may be heated and flow to the gas outlet 120b located at a higher position, thereby achieving gas convection. Therefore, the gas may flow faster into the gas inlet 120a. In another embodiment, the heating device 160 may be disposed near a gas inlet 120a of the gas channel 120. The gas may be heated and flow into the gas outlet 120b located at a higher position, to have the gas flowing faster into the gas inlet 120a. Compared with the conventional use of fan, the heating device 160 of the embodiment has a smaller size and is easier to be integrated on the substrate.

Figure 8B:
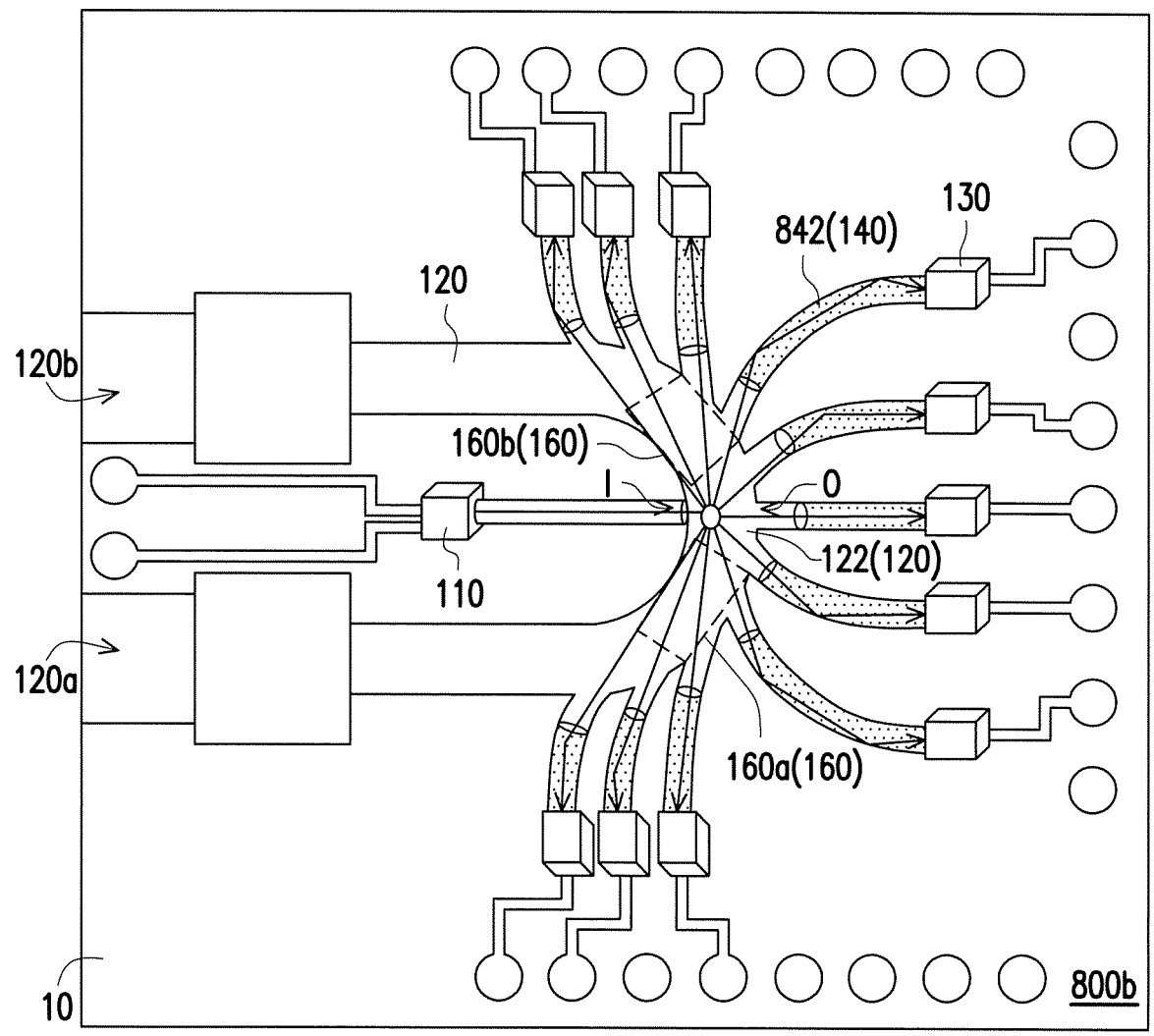
FIG. 8B is a top view of an optical micro-particle detector according to an embodiment of the disclosure.

FIG. 8B is a top view of an optical micro-particle detector according to an embodiment of the disclosure. The optical micro-particle detector 800b in FIG. 8B and the optical micro-particle detector 800a in FIG. 8A are similar. The difference is that, a heating device of the optical micro-particle detector 800b is disposed near a lower portion of the gas channel 120 corresponding to the light entrance I and is attached to the bottom surface of the gas channel 120. In one embodiment, the heating device 160 may be disposed on the lower portion near one side of the gas inlet 120a of the curved segment 122 in the gas channel 120, and is attached to the bottom surface of the gas channel 120. In another embodiment, the heating device 160 may be disposed on the lower portion near one side of the gas outlet 120b of the curved segment 122 in the gas channel 120, and is attached to the bottom surface of the gas channel 120.

Since the substrate may be a flexible substrate, the optical waveguide which is disposed on the flexible substrate may be also flexible. In addition, in the embodiments of the disclosure, the volume of the optical micro-particle detector can be further reduced by way of chip integration.

Figures 9, 10:
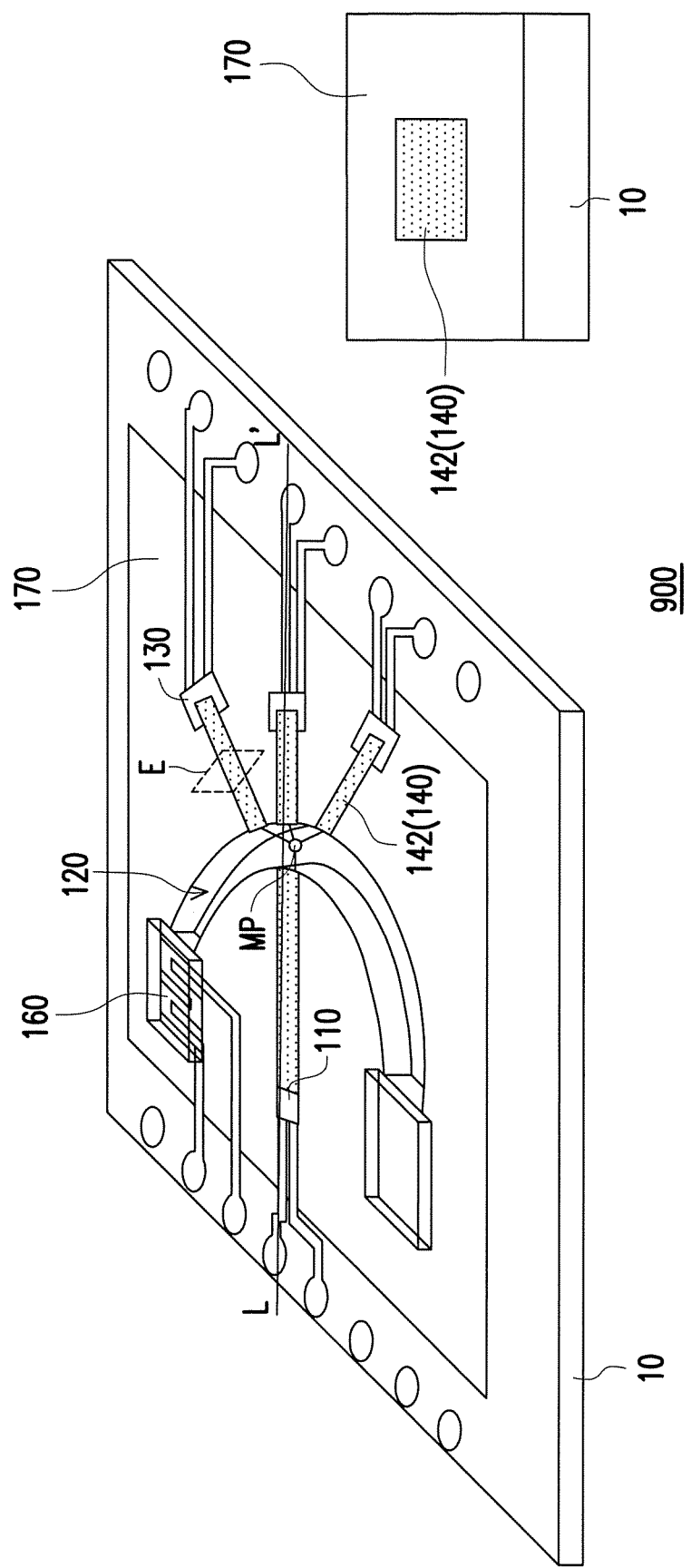
FIG. 9 is a perspective view of an optical micro-particle detector according to an embodiment of the disclosure.
FIG. 10 is a cross-sectional view taken along a cross section E of FIG. 9.
Figure 11:
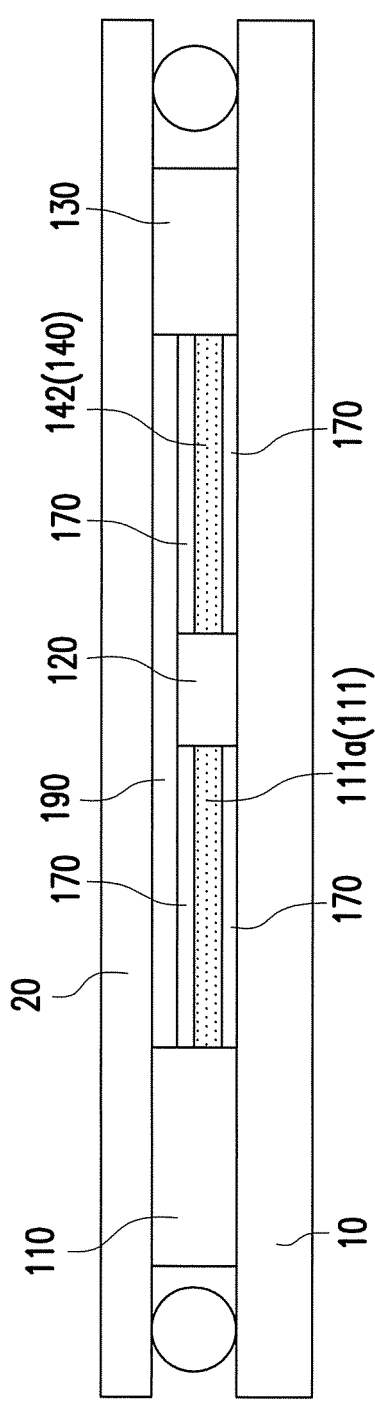
FIG. 11 is a first cross-sectional view taken along a line L-L' according to a first embodiment of FIG. 9.

FIG. 9 is a perspective view of an optical micro-particle detector according to an embodiment of the disclosure. FIG. 10 is a cross-sectional view taken along a cross section E of FIG. 9. FIG. 11 is a cross-sectional view of a first embodiment taken along the line L-L' of FIG. 9. Refer FIG. 9, FIG. 10 and FIG. 11, the optical micro-particle detector 900 in FIG. 9 and the optical micro-particle detector 800 in FIG. 8 are similar. In the embodiment of FIG. 9, the optical micro-particle detector 900 includes a cladding layer 170. The gas channel 120 and the plurality of the light channels 140 are located in the cladding layer 170. In addition, the light channel 140 between the light source 110 and the gas channel 120 is also disposed in the cladding layer 170. The light channel 111 may also contain the optical waveguide 111a. In the embodiment, a material of the cladding layer 170 may be Poly methyl methacrylate (PMMA). As shown in FIG. 10, the light channel 140 and the optical waveguide 142 are disposed in the cladding layer 170 in the cross section E which is perpendicular to an extending direction of the light channel 140. In one embodiment, as shown in FIG. 11, the optical micro-particle detector 900 may include a shielding cover 20 and an insulating layer 190. The shielding cover 20 is disposed on the light source 110, the gas channel 120, the plurality of the light channels 140, and the plurality of the optical detectors 130. The insulating layer 190 is disposed on the gas channel 120 and the plurality of the light channels 140, and under the shielding cover 20.

Figure 12:
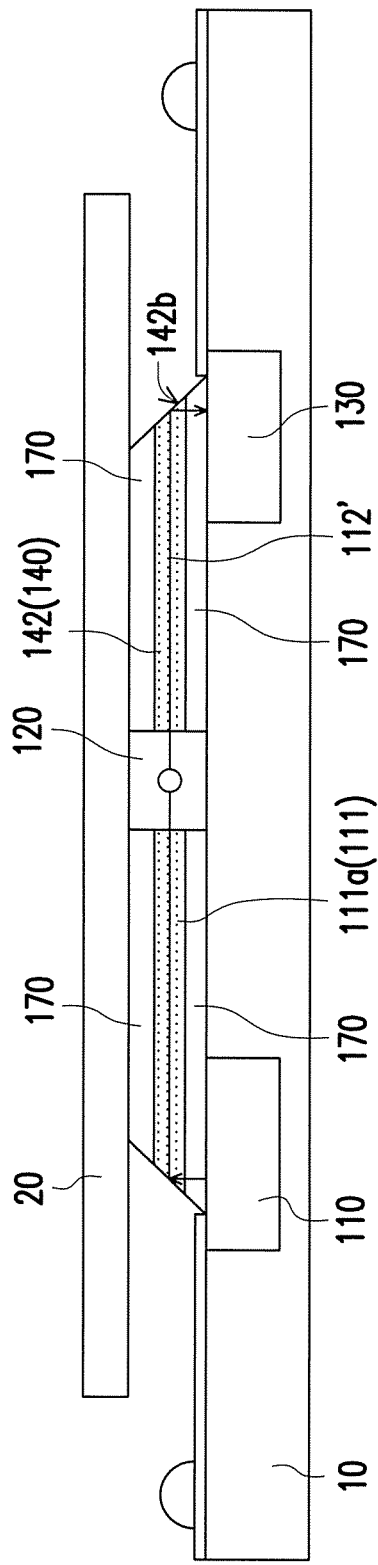
FIG. 12 is a cross-sectional view taken along line L-L' according to a second embodiment of FIG. 9.

FIG. 12 is a cross-sectional view of a second embodiment taken along the line L-L' of FIG. 9. Please refer to FIG. 11 and FIG. 12. In FIG. 11, the light source 110 and the plurality of the optical detectors 130 in the optical micro-particle detector 900 may be disposed on the substrate 10. The gas channel 120, the plurality of the light channels 140, and the plurality of the optical waveguides 142 are disposed on the substrate 10. In FIG. 12, the light source 110 and the plurality of the optical detectors 130 in the optical micro-particle detector 900 may be disposed in the substrate 10, that is, the light source 110 and the plurality of the optical detector 130 may be embedded in the substrate 10. The gas channel 120, the plurality of the light channels 140, and the plurality of the optical waveguides 142 are disposed on the substrate 10.

As shown in FIG. 12, in the embodiment, the optical waveguide 142 includes an inclined surface 142b. The inclined surface 142b is away from the gas channel 120 and may be used for reflecting light. Thus, the optical waveguide 142 does not need to be connected to the optical detector 130 directly, and the light beam 112' can be reflected onto the optical detector 130 by the inclined surface 142b. Therefore, the gas channel 120, the plurality of the light channels 140, and the plurality of the optical waveguides 142 can be disposed above the substrate 10, but not embedded in the substrate 10. It is easier for manufacturing.

Figure 13:
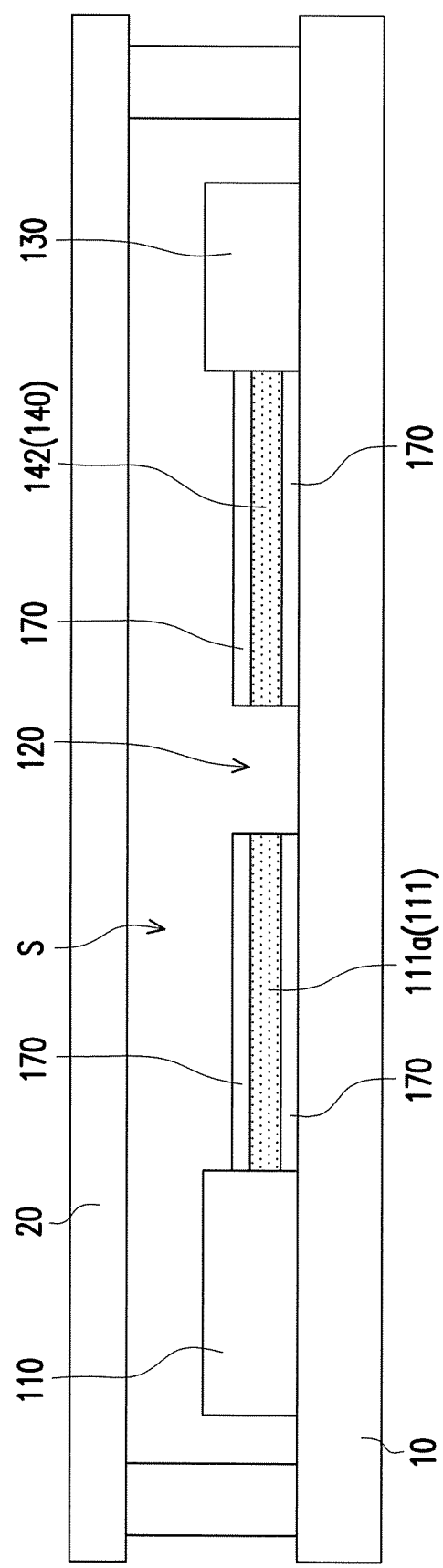
FIG. 13 is a cross-sectional view taken along line L-L' according to a third embodiment of FIG. 9.

FIG. 13 is a cross-sectional view of a third embodiment taken along line L-L' of FIG. 9. In FIG. 13, there is a space S between the shielding cover 20 and the gas channel 120, and the top of the gas channel 120 is opened and joins with the space S. In the present embodiment of FIG. 13, the position of a heating device, same as that of the heating device 160 in FIG. 8, may be located near the lower portion of the gas channel 120 corresponding to the light entrance I and is attached to the bottom surface of the gas channel 120. The gas may be heated and flows through the gas channel 120 and then flows towards the space S. This may also achieve gas convection.

Figure 14:
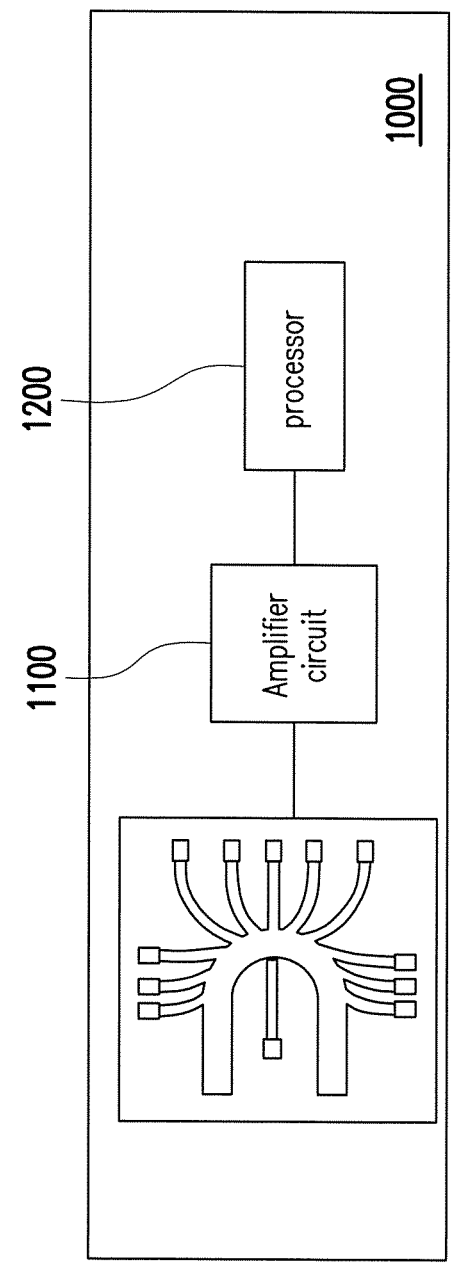
FIG. 14 is a structure diagram of an optical micro-particle detector according to an embodiment of the disclosure.

FIG. 14 is a structure diagram of an optical micro-particle detector according to an embodiment of the disclosure. An optical micro-particle detector 1000 includes a processor 1200 electrically connected to the plurality of the optical detectors 130. The processor 1200 depends on the plurality of the optical detectors 130 which detect the light beams 112' scattered by a plurality of micro-particles in the gas channel 120, and then calculates the concentration of the plurality of micro-particles. In the embodiment of FIG. 14, the optical micro-particle detector 1000 may further include an amplifier circuit 1100 electrically connected between the processor 1200 and the plurality of the optical detectors 130 for amplifying the electrical signals from the plurality of the optical detectors 130, and transmitting amplified electrical signals to the processor 1200.

In one embodiment, the processor 1200 may be, for example, a central processing unit (CPU), a microprocessor, a digital signal processor (DSP), a programmable controller, a programmable logic device (PLD) or other similar devices or combinations of these devices, but the scope of the disclosure is not to be limited thereto. In addition, in one embodiment, the processor 1200 may be implemented as a plurality of program codes to function. The plurality of program codes will be stored in a memory and executed by the processor 1200. Alternatively, in one embodiment, the processor 1200 may be implemented as one or more circuits to function. The processor 1200 may be implemented by software or hardware for functionalities, but the scope of the disclosure is not limited thereto.

In summary, according to the aforementioned embodiments, the optical micro-particle detector has at least one curved segment in the gas channel. Therefore, the light beam in lateral directions can be effectively detected by the plurality of the optical detectors in lateral directions after the light beam strikes the micro particles. Furthermore, since the at least one curved segment of the gas channel is a curved design, more optical detectors can be placed and the curved design also shortens the distances between these optical detectors in lateral directions and micro particles, so that the light beam in the lateral directions is less likely to strikes other micro particles before reaching the light exits O in the lateral directions and increase the accuracy of the light beam measurement. Besides, the optical waveguide is disposed at the inner side of the light channel and keeps a distance from its corresponding light exit, such that only the light beam closely parallel to an extending direction of the light channel 140 may be incident on the optical waveguide. This may prevent the interference of incident beams at other angles during the beam measurement. As a result, the optical micro-particle detector of the present invention can increase the accuracy of the light beam measurement.

According to the aforementioned embodiments of the optical micro-particle detector, the plurality of optical waveguides may guide the light beam through a total reflection principle. Thus, these optical waveguides may be curved and the loss energy of the light beam during scattering in the optical waveguides is not easily occurred, so that the plurality of optical waveguides can extend to farther locations. The plurality of optical detectors may be disposed near the edge of the substrate and be connected to external circuits without complicated wiring. This facilitates the integration of the chip. Besides, the heating device may be disposed in or beside the gas channel to replace the fan for gas convention. Accordingly, it is easier to reduce the volume of the optical micro-particle detector of the disclosure by way of chip integration.

It will be apparent to those skilled in the art that various modifications and variations can be made to the disclosed embodiments. It is intended that the specification and examples be considered as exemplary only, with a true scope of the disclosure being indicated by the following claims and their equivalents.

The invention claimed is:

1. An optical micro-particle detector, comprising:
a light source, configured to generate a light beam;
a gas channel having at least one curved segment, wherein the at least one curved segment has a light entrance and a plurality of light exits, and the light beam from the light source passes through the light entrance and enters the gas channel; and
a plurality of optical detectors, optically coupled to the plurality of light exits, respectively.

2. The optical micro-particle detector of claim 1, the at least one curved segment of the gas channel further comprising a first side wall and a second side wall, wherein the first side wall is opposed to the second side wall, the light entrance is disposed on one of the first side wall and the second side wall, and the plurality of the light exits are disposed on one of the first side wall and the second side wall.

3. The optical micro-particle detector of claim 2, wherein a disposition range of the plurality of the light exits in the at least one curved segment is within intersections of a tangent plane and the second side wall, and the tangent plane takes the light entrance as a point of tangency.

4. The optical micro-particle detector of claim 1, wherein the at least one curved segment of the gas channel is arc-shaped.

5. The optical micro-particle detector of claim 1, wherein the at least one curved segment of the gas channel is a plurality of connected curved segments, wherein curved directions of every two adjacent connected curved segments of the plurality of the connected curved segments are different from each other.

6. The optical micro-particle detector of claim 1, further comprising a plurality of light channels, the plurality of the light channels are optically coupled to the plurality of optical detectors, respectively, and to the plurality of light exits of the gas channel, respectively.

7. The optical micro-particle detector of claim 6, wherein the plurality of the light channels extend radially.

8. The optical micro-particle detector of claim 6, further comprising a cladding layer, wherein the gas channel and the plurality of the light channels are located in the cladding layer.

9. The optical micro-particle detector of claim 6, further comprising an insulating layer, wherein the insulating layer is disposed on the gas channel and the plurality of the light channels.

10. The optical micro-particle detector of claim 6, wherein each of the plurality of the light channels includes an optical waveguide, and the optical waveguide is disposed in the light channel and extends along an extending direction of the light channel.

11. The optical micro-particle detector of claim 10, wherein the optical waveguide is curved.

12. The optical micro-particle detector of claim 10, further comprising a light entrance surface, wherein the light entrance surface is located near the gas channel, and the light entrance surface is located on an inner side of the light channel and keeps a distance from its corresponding light exit.

13. The optical micro-particle detector of claim 10, wherein the optical waveguide further comprises a focus lens, and the focus lens is near a side of the gas channel and is integrated with the optical waveguide.

14. The optical micro-particle detector of claim 10, wherein the optical waveguide further comprises an inclined surface, and the inclined surface is away from the gas channel.

15. The optical micro-particle detector of claim 6, further comprising a shielding cover, wherein the shielding cover is disposed on the light source, the gas channel, the plurality of the light channels, and the plurality of the optical detectors.

16. The optical micro-particle detector of claim 15, wherein there is a space between the shielding cover and the gas channel, and a top of the gas channel is opened and joins with the space.

17. The optical micro-particle detector of claim 1, wherein the light source is a laser or a light emitting diode.

18. The optical micro-particle detector of claim 1, further comprising a heating device, wherein the heating device is disposed in or beside the gas channel.

19. The optical micro-particle detector of claim 1, further comprising a substrate, wherein the light source, the gas channel and the plurality of the optical detectors are disposed on the substrate.

20. The optical micro-particle detector of claim 19, wherein the plurality of the optical detectors are disposed near an edge of the substrate.

21. The optical micro-particle detector of claim 1, further comprising a substrate, wherein the gas channel is disposed on the substrate, and the light source and the plurality of the optical detectors are disposed in the substrate.

22. The optical micro-particle detector of claim 21, wherein the plurality of the optical detectors are disposed near an edge of the substrate.

* * * * *